(12) United States Patent
Maeda et al.

(10) Patent No.: US 6,544,554 B1
(45) Date of Patent: Apr. 8, 2003

(54) REGULATED RELEASE PREPARATIONS

(75) Inventors: Hiroyuki Maeda, Tokyo (JP); Yutaka Ogawa, Tokyo (JP); Yoshimitsu Iida, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/700,214

(22) PCT Filed: May 14, 1999

(86) PCT No.: PCT/JP99/02499

§ 371 (c)(1),
(2), (4) Date: Nov. 13, 2000

(87) PCT Pub. No.: WO99/59552

PCT Pub. Date: Nov. 25, 1999

(30) Foreign Application Priority Data

May 15, 1998 (JP) ............................................. 10-133219

(51) Int. Cl.[7] .................................................. A61K 9/22
(52) U.S. Cl. ........................ 424/468; 424/401; 424/464; 514/964
(58) Field of Search ................................ 424/401, 464, 424/468; 514/964

(56) References Cited

U.S. PATENT DOCUMENTS

| | | | |
|---|---|---|---|
| 4,822,808 A | * | 4/1989 | Iida et al. .................. 514/355 |
| 5,057,317 A | * | 10/1991 | Iida .............................. 424/423 |
| 5,188,840 A | | 2/1993 | Iida et al. |

FOREIGN PATENT DOCUMENTS

| | | |
|---|---|---|
| EP | 0 386 801 A2 | 9/1990 |
| EP | 0 470 047 A1 | 2/1992 |
| EP | 0 788 790 A2 * | 8/1997 |
| JP | 62-149630 A | 7/1987 |
| JP | 8-99906 A | 4/1996 |
| JP | 2638604 B2 | 4/1997 |
| JP | 9-221416 A | 8/1997 |

* cited by examiner

Primary Examiner—Jose' G. Dees
Assistant Examiner—Konata M. George
(74) Attorney, Agent, or Firm—Browdy and Neimark, PLLC

(57) ABSTRACT

Controlled-release formulation having such a portion that the core and a drug release layer each of which has been formulated to effect rapid or gradual release of at least one drug the release of which is to be controlled is covered either partly or entirely with a release control layer that is produced by adding pharmaceutically acceptable additives to at least one base selected from among fumaric acid, DL-tryptophan and L-tyrosine and which is substantially free from the drugs the release of which is to be controlled.

19 Claims, 4 Drawing Sheets

RELEASE TIME LAG VS. STEARIC ACID ADDITION

REGULATED RELEASE PREPARATIONS

CROSS REFERENCE TO RELATED APPLICATION

The present application is the national stage under 35 U.S.C. 371 of PCT/JP99/02499, filed May 14, 1999.

TECHNICAL FIELD

This invention relates to a multiple-release formulation and a process for producing it. The invention relates particularly to a formulation that has a drug core surrounded by a release control layer to present a mechanism by which the drug in the core is rapidly released after a predetermined delay in time. The invention further; relates to a formulation which also has a rapid drug release portion provided outside the release control layer so that the drug can be released more than once at intervals after single dosing. Further in addition, the invention relates to a formulation that incorporates a plurality of drugs in both a core and one or more drug release layers so that different active ingredients can be released at different times.

BACKGROUND ART

Oral controlled-release formulations have the advantage of reducing the frequency of dosing so that the burden on patients is reduced to improve their compliance. As examples of the technology for oral controlled-release formulations, sol-called sustained-release formulations which release the drug in a sustained manner to main therapeutic blood levels are widely known (e.g. sustained-release theophylline formulation "Theo-Dur" and slow-release propranolol hydrochloride formulation). A problem with such sustained-release formulations that maintain the drug blood level within the therapeutic range before excretion is that some drugs have a high likelihood for developing tolerance. As a further problem, drugs that are sensitive to first-pass metabolism in the liver have lower bioavailability when administered in the sustained-release dosage form than when they are administered in immediate-release dosage forms. These kinds of drugs are effectively administered in formulations that provide more than one release by single dosing. It is sometimes desired that two drugs be allowed to act by administering them at different times as in a case where the therapeutic effect of one drug can be improved by a preliminary or post-treatment with the other drug; in these situations, it is effective to use controlled-release formulations that allow for more than one release of different drugs at different times after single dosing.

As far as the present inventors know, the conventional pharmaceutical formulation techniques that allow for more than one drug release with a view to reducing the frequency of dosing include the use of matrix-forming water-soluble polymers or waxes as a release control base that surround the drug core containing a water-swellable disintegrant (see, for example, Japanese Patent Public Disclosure Nos. 246512/1987 and 273816/1992). However, the water-soluble polymer base is difficult to use with drugs that are labile in the presence of water in the polymer base. The matrices made of waxes are so labile under elevated temperatures that the drug release characteristics may potentially change during storage. What is more, waxes cannot generally be applied to drugs that are either reactive or miscible with them. Thus, no multiple-release formulations have been developed that can be applied to control the release of a broader range of drugs and which do not experience any change in drug release characteristics during storage.

DISCLOSURE OF THE INVENTION

In view of these problems of the prior art, the present invention aims at providing a formulation that uses a release controlling non-wax base of which the water content can be easily controlled and which permits more than one drug release, that is capable of precise control over the time interval (or "time lag") between individual releases, and that is less sensitive to the environment in the gastrointestinal tract. The invention also aims at providing a technology for producing the formulation.

The present inventors made intensive studies in order to solve the above-mentioned problems of the prior art. As a result, they found that when at least one low-molecular weight substance having low dissolution rate under physiological conditions as selected from among fumaric acid, DL-tryptophan and L-tyrosine was incorporated as a base for a release control layer in a formulation, it was not only easy to control the water content of the base but controlled drug release with desired time lag could also be achieved without using waxes as the release control base. The present invention has been accomplished on the basis of this finding.

Hence, the present invention provides a controlled-release formulation that comprises essentially a core containing at least one drug the release of which is to be controlled, a release control layer that is produced by adding pharmaceutically acceptable additives to at least one base selected from among fumaric acid, DL-tryptophan and L-tyrosine and which is a coating layer substantially free of drugs the release of which is to be controlled, and a drug release layer that contains at least one drug the release of which is to be controlled, said formulation satisfying the following conditions:

(1) the core be located in the innermost portion of the controlled-release formulation;

(2) said formulation have at least one release control layer covering the core, with at least one additional release control layer and/or drug release layer being optionaly present;

(3) the release control layer(s) alternate with the drug release layer(s);

(4) the outermost layer may be either the release control layer or the drug release layer;

(5) if the outermost layer is the drug release layer, it may cover all or part of the surface of the underlying release control layer;

(6) the drugs to be contained in the core and the drug release layer of said formulation should be selected independently of each other;

(7) the core and the drug release layers may be formulated to permit immediate release or slow release of the drugs contained; and (8) if two or more drugs are to be contained in the core and the drug release layer(s) of said formulation, said core and a single drug release layer may each be composed of more than one layer containing only one drug.

Thus, according to the present invention, there is provided a controlled-release formulation having such a portion that a core formulated to permit rapid or slow release of one or more drugs is covered with a release control layer that is prepared by adding pharmaceutically acceptable additives to at least one base selected from among fumaric acid, DL-tryptophan and L-tyrosine and which is substantially free from the drugs the release of which is to be controlled.

The present invention also provides a process for producing a controlled-release formulation that comprises at least the following step A:

A. molding a core containing at least one drug the release of which is to be controlled and forming a release control layer by covering said core with a component that has a pharmaceutically acceptable additive incorporated in at least one base selected from among fumaric acid, DL-tryptophan and L-tyrosine and which is substantially free of the drugs thee release of which is to be controlled and thereby forming a shape of a dual structure;

said step A being optionally followed by the following step B, or the following steps B and C, or the following steps B–D, or the following steps B–E:

B. covering or overlaying the shape of a dual structure with a component containing at least one drug the release of which is to be controlled and thereby forming a drug release layer;

C. covering the shape obtained in said step B with a component that has a pharmaceutically acceptable additive incorporated in at least one base selected from among fumaric acid, DL-tryptophan and L-tyrosine and which is substantially free from the drugs the release of which is to be controlled and thereby forming a release control layer;

D. covering or overlaying the shape obtained in said step C with a component containing at least one drug the release of which is to be controlled and thereby forming a drug release layer; and E. repeating said step C of forming a release control layer and said step D of forming a drug release layer at least once to produce the desired controlled-release formulation which satisfies the above-mentioned conditions (1)–(8).

BEST MODE FOR CARRYING OUT THE INVENTION

The controlled-release formulation of the invention may be structured in any fashion as long as it satisfies the above-mentioned conditions (1)–(8). It comprises a unit consisting of at least two structural portions, namely, a core formulated to permit rapid or slow (sustained) release of at least one drug the release of which is to be controlled (i.e., there is a core portion that contains the drug(s) the release of which is to be controlled and which is located in the innermost part of the formulation) and a release control layer that is substantially free from the drug(s) the release of which is to be controlled and which covers the core to control the time lag for drug release from the core (see FIG. 1).

Figure 2:
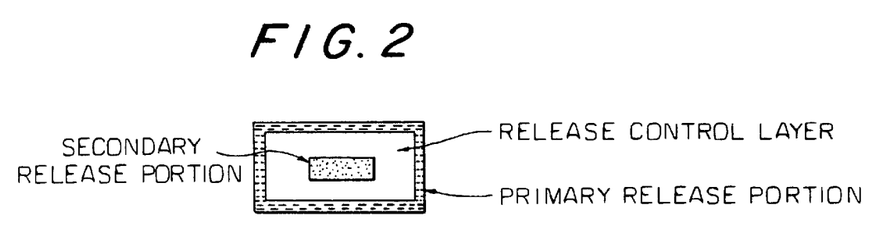
FIG. 2 is a schematic for a tablet which is another example of the controlled-release formulation of the invention and which has the release control layer surrounded by a primary release component (a drug release layer)
Figure 3:
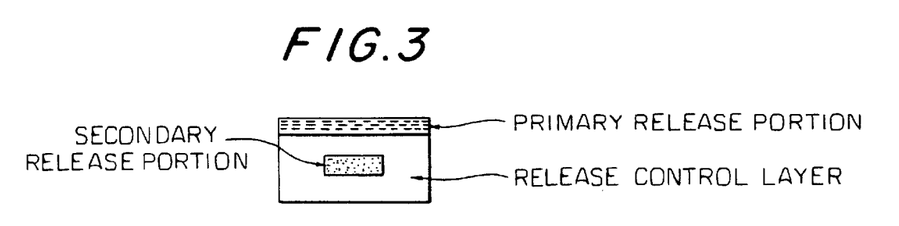
FIG. 3 is a schematic for a tablet which is still another example of the controlled-release formulation of the invention and which has the release control layer overlaid (its surface partly covered) with a primary release component (a drug release layer)

The multiple-release formulation of the invention consists of at least three structural portions, namely, a core that contains a drug the release of which is to be controlled and which releases the drug after a predetermined time lag (i.e., the core is a secondary release portion located in the innermost part of the formulation), a release control layer that is substantially free from the drug the release of which is to be controlled and which covers the core to control the time lag for drug release from the core, and a drug release layer (a primary release portion) that contains a drug which is the same as or different from the drug the release of which is to be controlled and which covers all surface of the release control layer (see FIG. 2) or overlays it (partly covers it as shown in FIG. 3) so as permit rapid or sustained (slow) release of the contained drug after dosing. If the formulation shown in FIG. 2 or 3 is dosed, a first drug release occurs from the drug release layer (primary release portion) and a second drug release occurs from the core (secondary release portion) after a predetermined time lag, thus allowing for two drug releases by single dosing.

Figure 4:
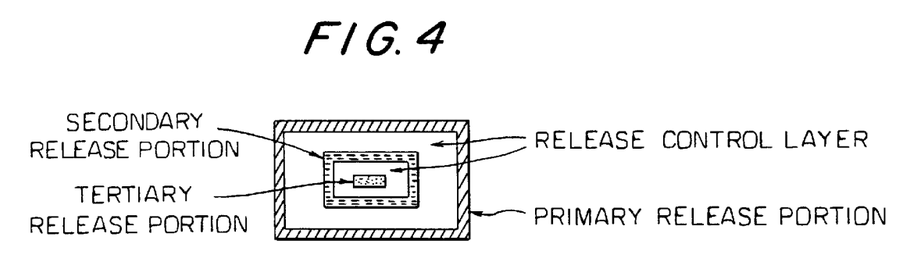
FIG. 4 is a schematic for a tablet which is yet another example of the controlled-release formulation of the invention and which has a core of the tablet of FIG. 2, with the release control layer being covered with a primary release component (a drug release layer) to permit three drug releases.
Figure 5:
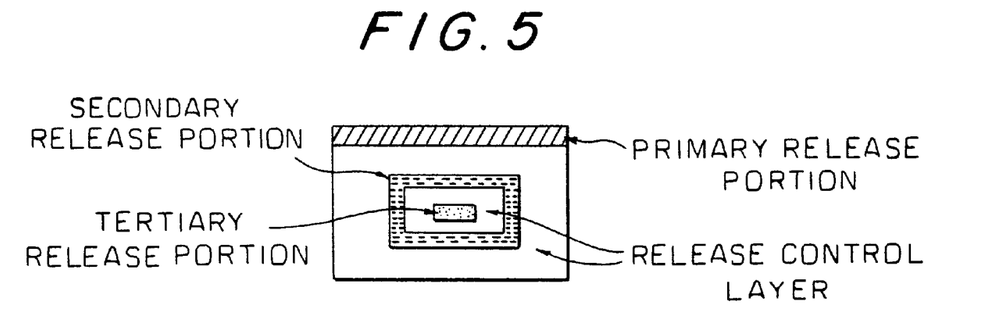
FIG. 5 is a schematic for a tablet which is still another example of the controlled-release formulation of the invention and which has a core of the tablet of FIG. 2, with the release control layer being overlaid (its surface partly covered) with a primary release component (a drug release layer) to permit three drug releases.

The present invention encompasses a formulation consisting of five structural portions such that the outer surface of the unit shown in FIG. 2 is covered with a secondary release control layer that is substantially free from the drug the release of which is to be controlled, the outer surface of said secondary release control layer being entirely covered with a drug release layer (FIG. 4) or overlaid with it (partly covered with it as shown in FIG. 5). If the formulation shown in FIG. 4 or 5 is dosed, a first drug release occurs from the outermost drug release layer (the primary release portion), a second drug release occurs from the second drug release layer (the secondary release portion) after a predetermined time lag, and a third drug release occurs from the core (the tertiary release portion) a predetermined time lag after the second release, thus allowing for three drug releases by single dosing.

While the foregoing description concerns three cases of the controlled-release formulation, one consisting of two structural portions, another consisting of three structural portions, and the third consisting of five structural portions, the numbers of the release control layers and the drug release layers that can be incorporated in the controlled-release formulation of the invention are in no way limited. The outermost layer may be either a drug release layer or a release control layer.

The core and the drug release layer(s) may be formulated as an immediate-release or slow-release type depending upon the specific use of the formulation. If the controlled-release formulation of the invention has drug release layers, the drug to be contained in the core may be the same as or different from the drug(s) to be contained in the drug release layers. Referring to the formulation shown in FIG. 4 which consists of five structural portions, the following combinations of drugs may be presented:

Combination 1: primary release portion→A, secondary release portion→A, tertiary release portion→A Combination 2: primary release portion→A, secondary release portion→B, tertiary release portion→C Combination 3: primary release portion→A, secondary release portion→B, tertiary release portion→A Combination 4: primary release portion→A and B, secondary release portion→A and B, tertiary release portion→A and B Combination 5: primary release portion→A and B, secondary release portion→A, tertiary release portion→A and B Combination 6: primary release portion→A and B, secondary release portion→A, tertiary release portion→A and C In these examples, the primary release portion means the outermost drug release layer, the secondary release portion means the second drug release layer, and the tertiary release portion means the core; A, B and C represent three different drugs.

In combinations 1 and 4, the same kind of drug is released from each release portion and this type of formulations release the same active ingredient multiple times (and commonly called a "pulsed" type). Formulations of "pulsed" type offer the following great benefits. If drugs such as nicorandil, nifedipine and propranolol hydrochloride are formulated as a pulsed type, worsening of the disease state by noncompliance can be suppressed and the side effects of the conventional slow-release formulations such as headache and chill can be reduced. If drugs such as metoclopramide hydrochloride are formulated as a pulsed type, patients can have their quality of life (QOL) improved by reducing the frequency of administration. If drugs such as procaterol hydrochloride are formulated as pulsed type, patients with bronchial asthma can have their QOL improved since they suffer fewer attacks at dawn.

If different drugs are released from different release portions as in combinations 2, 3, 5 and 6, different active ingredients can be released at desired time intervals. Combination 5 has a particular advantage in that combination therapy of A which is dosed three times a day and B which is dosed twice a day can be replaced by single daily dosing. Combination 6 has a particular advantage in that combination therapy of A which is dosed three times a day and B and C which are each dosed once a day can be replaced by single daily dosing. Combining different drugs in these ways, one can expect prevention of the reduction in drug activities and the occurrence of side effects due to missing a dose of either one of the drugs that must be taken at different time intervals or taking a wrong drug.

In the present invention, the time lag of drug release from the core is controlled by the disintegration time of the release control layer and in order for it to be disintegrated in a predetermined time (typically from several hours to ten-odd hours) after dosing, a low-molecular weight substance that dissolves slowly under physiological conditions must be used as the base for the release control layer. Examples of such low-molecular weight substance include fumaric acid, DL-tryptophan and L-tyrosine and one or more of these substances can be used as the base(s). These substances are incorporated in the release control layer in amounts that typically range from 60 to 99%, preferably from 75 to 98%, more preferably from 90 to 95%. If they are used in amounts of less than 60%, the release control layer disintegrates so rapidly after dosing that the desired time lag is not obtained. If they are used in amounts of more than 99%, the molding property deteriorates to pose problems such as variations in time lag from one lot of tablets to another.

Figure 1:
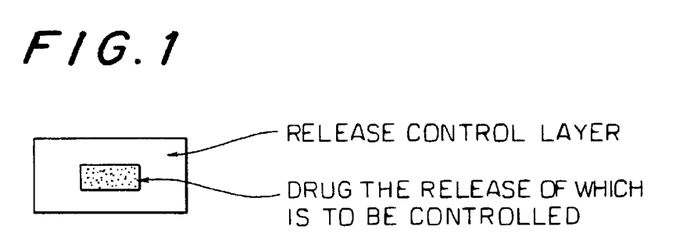
FIG. 1 is a schematic for an example of the controlled-release formulation of the invention which consists of a core containing a drug the release of which is to be controlled and a release control layer.

In order to prepare the multiple-release formulation of the invention, the core is first shaped, then mixed with the ingredients for the release control layer and compressed with a suitable tablet machine such as a dry coating machine to produce a dual-structured shape having the core coated with the release control layer (see FIG. 1). The dual-structured shape may be covered with the ingredients for the immediate-release portion by means of a suitable machine such as a coating machine (see FIG. 2) or, alternatively, the release control layer may be overlaid with the immediate-release portion under pressure on a tablet machine (see FIG. 3). Either method can produce a double-release formulation. The above-mentioned methods may be utilized such that the shape depicted in FIG. 2 is mixed with the ingredients for the second release control layer and compressed with a suitable tablet machine such as a dry coating machine to produce a triplex-structured shape which is then covered with the ingredients for the immediate-release portion by means of a suitable machine such as a coating machine (see FIG. 4) or, alternatively, the second release control layer may be overlaid with the immediate-release portion under pressure on a tablet machine (see FIG. 5). Either method can produce a triple-release formulation. As will be apparent from the above description, the critical point for the manufacture of the multiple-release formulation of the invention is to prepare the dual-structured shape depicted in FIG. 1. On the pages that follow, the method of preparing the dual-structured shape is described in detail assuming that fumaric acid is used as the base for the release control layer.

The first step in the method is to make a core of the drug the release of which is to be controlled. The core can be formulated such that the drug is released in a mode or at a rate that is therapeutically desirable. While there are no particular limitations on the size and shape of the core, it is desirably as small as possible to provide ease of dosing since it is ultimately covered with the release control layer.

The shape of the core may resemble a tablet, a capsule, a granule or any other dosage form and there are no particular limitations on the core shape that can be employed as long as it is suitable for the physicochemical properties of the drug contained in the core and does not cause a change in the release characteristics of the drug during the step of shaping the release control layer.

In a separate step from the shaping of the core, fumaric acid is comminuted and the resulting powder as the principal feed is mixed with a binder and an excipient and granulated. Fumaric acid can be comminuted by known methods including dry processes such as jet milling, hammer milling, pin milling and ball milling or wet methods and various techniques can be employed without limitations. The size of the fumaric acid particles affects the time lag for release control. In order to extend the time lag, the particle size of the fumaric acid powder must be sufficiently small, preferably 100 $\mu$m or less, preferably 50 $\mu$m, on average. The fumaric acid granulation can be prepared by any known methods such as high shear granulation, fluid-bed granulation, tumbling fluid-bed granulation, spray drying and extrusion granulation and various techniques can be employed without limitations.

In the next step, pharmaceutically acceptable additives are added and uniformly mixed with the fumaric acid granules to prepare a blended granulation. This blended granulation as well as the previously formulated core are loaded into a suitable tablet machine such as a dry coating machine and the two materials are compressed into a dual-structured shape having the core covered with the release control layer.

The drugs the release of which can be controlled in accordance with the invention are not limited to any particular types and may include nifedipine, propranolol hydrochloride, nicroandil, metoclopramide hydrochloride, procaterol hydrochloride and any other drugs that would benefit from more than one release after single dosing.

While the process for producing the multiple-release formulation of the invention has been described above with reference to a tablet, it should be noted that tablet is not the sole example of the dosage forms for the controlled-release formulation of the invention and it can be prepared as any kind of solid formulations.

EXAMPLES

The following examples are provided for the purpose of further illustrating the present invention but are in no way to be taken as limiting its scope.

Example 1

Preparing Fumaric Acid Granules

Fumaric acid granules consisting of fumaric acid, anhydrous calcium hydrogenphosphate and corn starch were prepared from the following composition.

| Ingredient | Proportion (%) |
| --- | --- |
| Fumaric acid | 91.05 |
| Anhydrous calcium hydrogenphosphate | 6.67 |
| Corn starch | 2.28 |

After preliminary treatment with a wet comminuting mill "Micolloider", fumaric acid was mixed with the other ingredients to form a slurry which was supplemented with water and subjected to spray drying to prepare fumaric acid granules having an average size of 150–250 μm.

In a separate step, dye blue No. 1 was chosen as a model ingredient and core tablets were prepared from the following composition. A paste containing corn starch at a concentration of 10% was added to the other ingredients except calcium stearate and thoroughly mixed with a Shinagawa Universal Mixer Agitator. The resulting pellets were made uniform in size on a speed mill, dried, mixed with calcium stearate and fed into a tablet machine so as to prepare 4 mmφ tablets with beveled edges.

| Ingredient | Amount (mg per tablet) |
| --- | --- |
| Pigment blue No. 1 | 1.2 |
| Mannitol | 35 |
| Croscarmellose sodium | 2.65 |
| Corn starch | 0.85 |
| Calcium stearate | 0.3 |
| Subtotal | 40 |

For each tablet, 376 mg of the fumaric acid granules, 20 mg of stearic acid and 4 mg of calcium stearate were mixed and fed into a dry coating machine (Kikusui Seisakusho), where the powder mixture was compressed into 8.5 mmφ controlled-release tablets, with the coat of the powder mixture being properly adjusted to ensure that the core tablet containing dye blue No. 1 would be located in the center of each controlled-release tablet.

Example 1 concerns the case of producing controlled-release tablets using fumaric acid as the base for the release control layer. Selected samples of the tablets were split into halves along the diameter to confirm that the core tablet had the shape shown in FIG. 1.

Example 2

Discoid tablets having a diameter of 5 mm were prepared from the following composition using nicorandil as the drug substance in the core tablet.

| Ingredient | Amount (mg per tablet) |
| --- | --- |
| Nicorandil | 5.0 |
| Mannitol | 37.2 |
| Stearic acid | 4.0 |
| Croscarmellose sodium | 2.4 |
| Corn starch | 1.1 |
| Calcium stearate | 0.3 |

Fumaric acid granules were prepared in accordance with Example 1; 470 mg per tablet of the granules were mixed with 25 mg of stearic acid and 5 mg of calcium stearate, both being used as a lubricant, to prepare a powder mixture. The nicorandil containing core tablets and the powder mixture were fed into a tablet machine of the same type as used to prepare the controlled-release tablets in Example 1 and compressed to prepare 9.5 mmφ controlled-release tablets.

Figure 6:
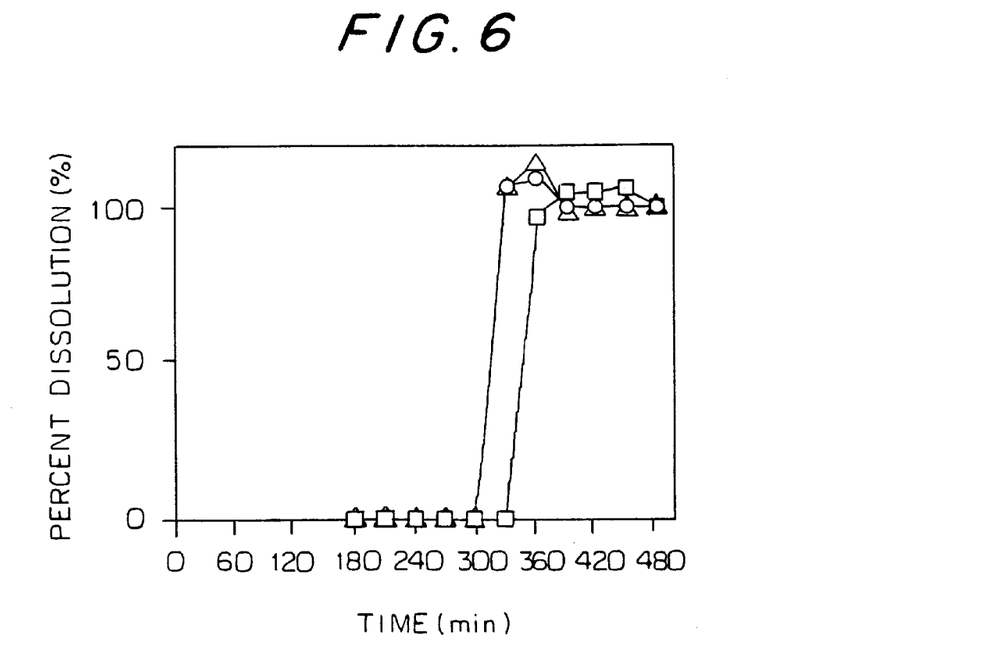
FIG. 6 is a graph showing the result of the release test conducted in Example 2.

Test fluids containing the tablets prepared in Example 2 were subjected to a dissolution test in 500 mL of water at 37° C. in accordance with Method 1 described in the Japanese Pharmacopoeia. Samples of the test fluids were taken at given intervals and the content of nicorandil in each sample was measured by HPLC to give the results shown in FIG. 6, from which one can see that abrupt drug release occurred after specified time delays (time lag). In FIG. 6, symbols ○, Δ and □ designate the results of the dissolution test on three different tablets from the same lot.

Example 3

In Example 2, stearic acid was used as a lubricant and represented 5% of the constituents in the release control layer. In Example 3, powder mixtures were prepared at varying stearic acid contents of 0%, 5%, 10% and 15% and compressed as in Example 2 to prepare four kinds of controlled-release tablet.

Figure 7:
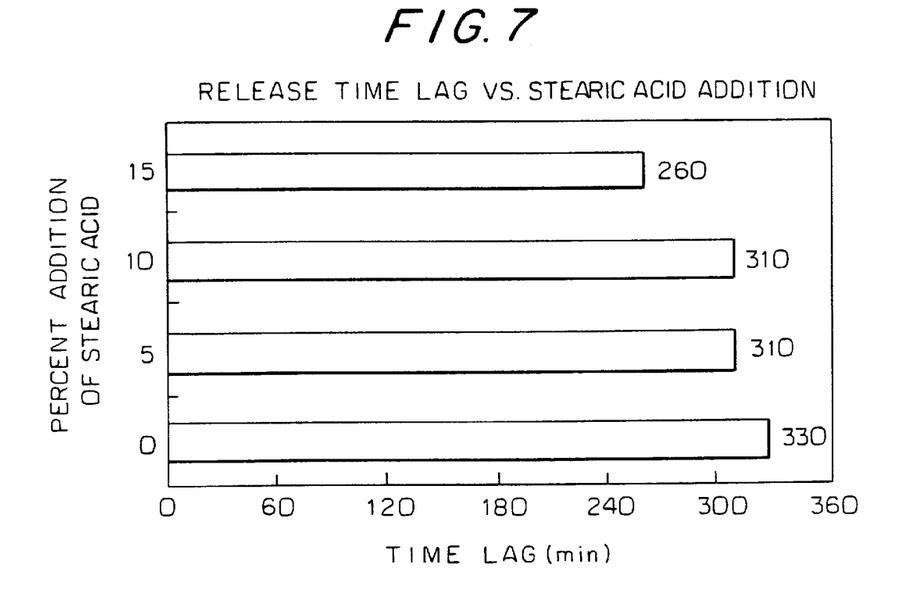
FIG. 7 is a graph showing the result of the release test conducted in Example 3.

FIG. 7 compares the time lag of the controlled-release tablets having different contents of stearic acid in the coat. Obviously, incorporating stearic acid had little effect on the control of drug release and an adequately extended time lag could be realized by not incorporating stearic acid. It was therefore demonstrated that the fundamental mechanism for drug release control in the present invention was ascribable not to wax but to the base for the release control layer. The data shown in FIG. 7 was obtained by the same method as used in Example 2; the amount of nicorandil that dissolved out was measured over time and the time during which no more than 5% dissolution occurred was designated "time lag".

Example 4

Propranolol hydrochloride was chosen as the drug the release of which was to be controlled by the invention and discoid core tablets having a diameter of 5 mm were prepared from the following composition.

| Ingredient | Amount (mg per tablet) |
| --- | --- |
| Propranolol hydrochloride | 10.0 |
| Lactose | 30.15 |
| Crystalline cellulose | 8.0 |
| Corn starch | 1.6 |
| Mg stearate | 0.25 |
| Total | 50.0 |

Fumaric acid granules were prepared in accordance with Example 1; 470 mg per tablet of the granules were mixed with 25 mg of stearic acid and 5 mg of calcium stearate, both being used as a lubricant, to prepare a powder mixture. The propranolol containing core tablets and the powder mixture were fed into a tablet machine of the same type as used to prepare the controlled-release tablets in Example 1 and compressed to prepare 9.5 mmφ controlled-release tablets.

Figure 8:
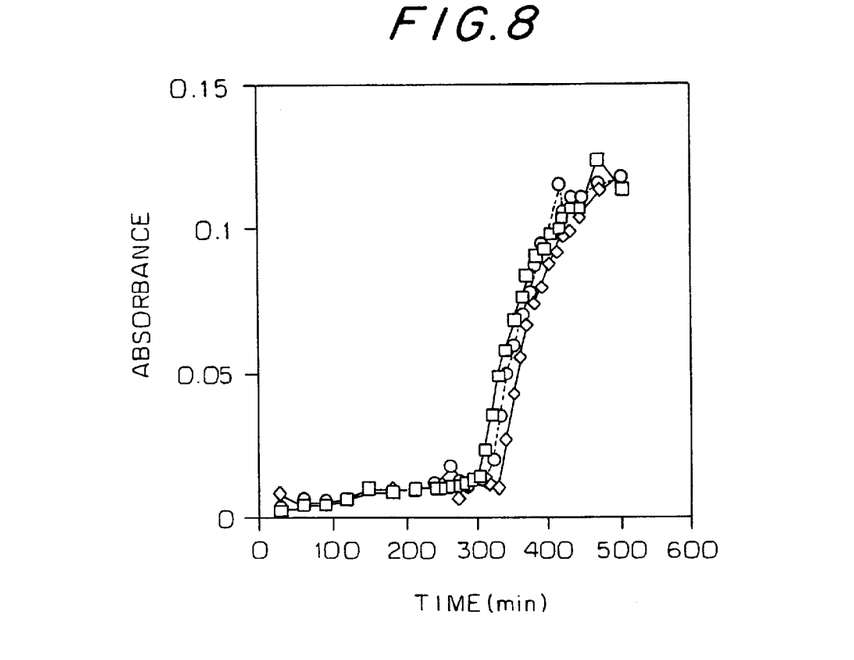
FIG. 8 is a graph showing the result of the release test conducted in Example 4.

The controlled-release tablets prepared in Example 4 contained propranolol as the drug the release of which was to be controlled. The dissolution rate of the tablets was also evaluated under the same conditions as in Example 2 and it was shown that they started to release the drug substance after a certain time lag (see FIG. 8). In FIG. 8, symbols ○, ◇ and □ designate the results of the dissolution test on three different tablets from the same lot.

Example 5

Three hundred milligrams of fumaric acid granules as prepared in accordance with Example 1 were lightly formed into a concave shape using a mold in discoid shape of o.d. 8.5 mm with beveled edges and embossed at the center in a diameter of 4 mm. The central cavity in each shape was filled with 20 mg of a 1:3 powder mixture of nicorandil chosen as the drug the release of which was to be controlled and the dispersant crystalline cellulose. The filling was overlaid with 100 mg of the previously prepared fumaric acid granules and compressed into 8.5 mmφ round tablets.

It was thus shown in Example 5 that the method of the invention was feasible without using tablets as the core and that the drug in the core the release of which was to be controlled was by no means limited in terms of dosage form.

Example 6

Fumaric acid granules were prepared in accordance with Example 1 and 470 mg per tablet of the granules were mixed with 25 mg of stearic acid and 5 mg of calcium stearate, both being used as a lubricant, to prepare a powder mixture. In another run, 517 mg per tablet of the fumaric acid granules were mixed with 27.5 mg of stearic acid and 5.5 mg of calcium stearate, both being used as a lubricant, to prepare a powder mixture. Either of these powder mixtures as well as the nicorandil-containing core tablets prepared in accordance with Example 2 were compressed at varying pressures to prepare tablets having average time lags of 140, 250 and 365 minutes in a dissolution test (in vitro).

Figure 9:
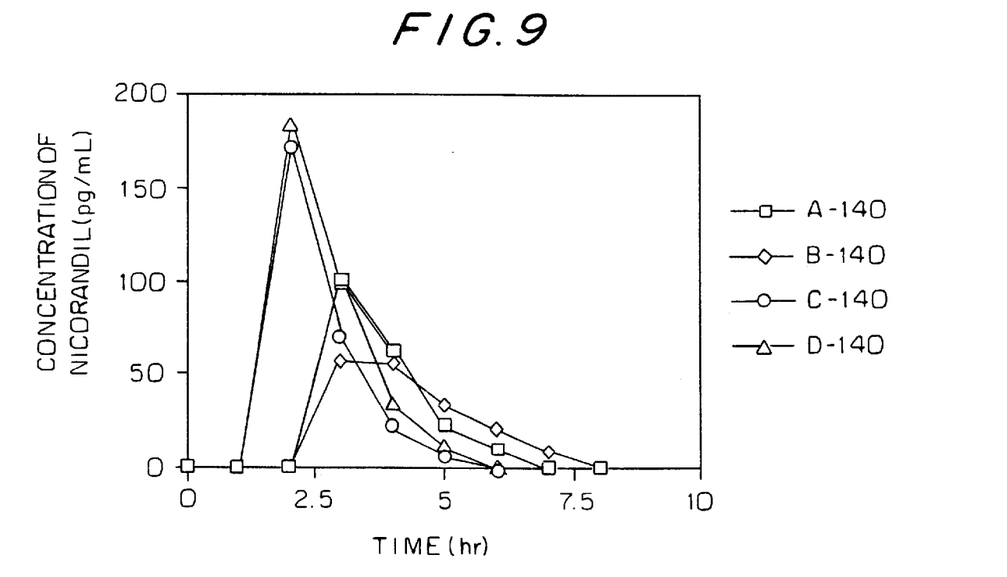
FIG. 9 is a graph representing the results of the absorption time lag measurements conducted in Example 6.
Figure 10:
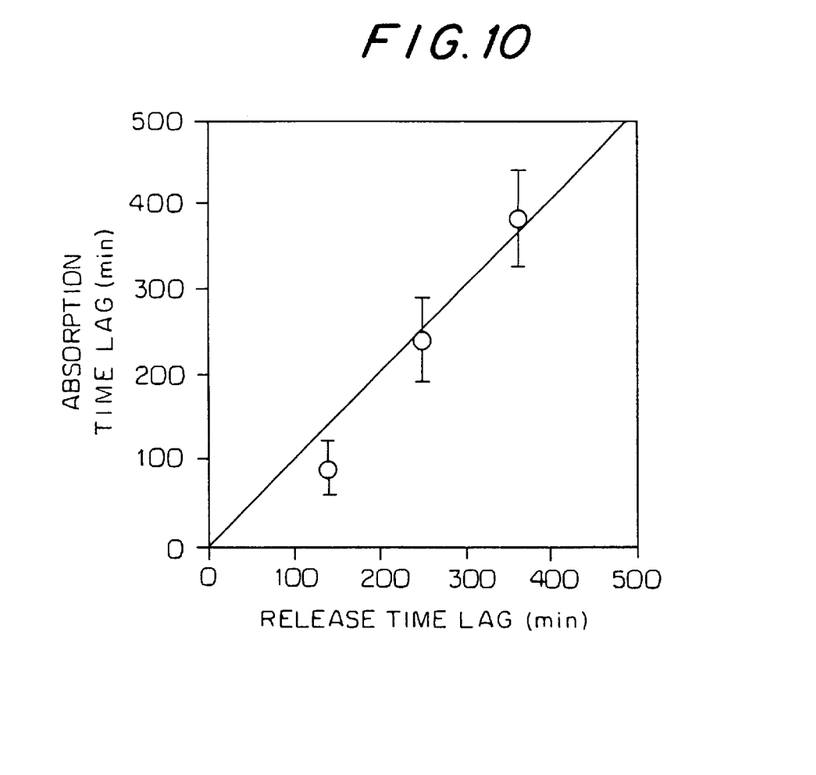
FIG. 10 is a diagram showing the correlation between release time lag and absorption time lag as observed in Example 6.

A group of beagles were administered the nicorandil containing formulations of Table 6 and their blood was sampled every hour. The time required for the first drug appearance to occur in the blood was counted as an absorption (in vivo) time lag and evaluated for correlation to the three release time lag. In view of the good positive relationship, nicorandil also had a time lag for release in vivo. Representative serum-drug concentration curves from four dogs are shown in FIG. 9 and the relationship between the absorption time lag and each of the three tested release time lags is shown in FIG. 10.

The above data demonstrates the preparation of formulations that permit the drug substance to be released after desired time lags the length of which is less sensitive to the environment in the digestive tract.

INDUSTRIAL APPLICABILITY

As described above, the present invention reduces the frequency of drug dosing to thereby improve the patient compliance; as a result, one can reduce the frequency of dosing of certain drugs which have heretofore been held difficult to be prepared as slow-release formulations since they are suspected of inducing the development of tolerance. In certain therapeutic regimens, a first drug release is designed to enhance an efficacy of secondary releasing drug and this can be accomplished by single dosing in accordance with the present invention.

In the controlled-release formulation of the invention, the time lag for drug release can be set to a desired value by appropriately adjusting the relative proportions of the low-molecular weight base for controlled release and the binder, the amount of the release control layer, the shape of tablet, and the compression pressure if the dosage form is a tablet.

What is claimed is:

1. A controlled-release formulation that comprises essentially a core containing at least one drug the release of which is to be controlled, a release control layer that is produced by adding pharmaceutically acceptable additives to at least one base selected from among fumaric acid and DL-tryptophan and which is a coating layer substantially free of drugs the release of which is to be controlled, and a drug release layer that contains at least one drug the release of which is to be controlled, said formulation satisfying the following conditions:

(1) the core be located in the innermost portion of the controlled-release formulation;

(2) said formulation have at least one release control layer covering the core, with at least one additional release control layer and/or drug release layer being optionally present;

(3) the release control layer(s) alternate with the drug release layer(s);

(4) the outermost layer be either the release control layer or the drug release layer;

(5) if the outermost layer is the drug release layer, it may cover all or part of the surface of the underlying release control layer;

(6) the drugs to be contained in the core and the drug release layer of said formulation should be selected independently of each other;

(7) the core and the drug release layers be optionally formulated to permit immediate release or slow release of the drugs contained; and (8) if two or more drugs are to be contained in the core and the drug release layer(s) of said formulation, said core and a single drug release layer optionally each be composed of more than one layer containing only one drug.

2. The controlled-release formulation according to claim 1, whose dosage form is a solid preparation.

3. The controlled-release formulation according to claim 2, whose dosage form is a tablet.

4. The controlled-release formulation according to claim 1, which contains an immediate-release portion.

5. The controlled-release formulation according to claim 4, whose core comprises the immediate-release portion.

6. The controlled-release formulation according to claim 4, wherein the immediate-release portion contains a different drug from the drug the release of which is to be controlled.

7. The controlled-release formulation according to claim 1, wherein the base is fumaric acid.

8. The controlled-release formulation according to claim 1, wherein the base is DL-tryptophan.

9. A process for producing a controlled-release formulation that comprises at least the following step A:

A. molding a core containing at least one drug the release of which is to be controlled and forming a release control layer by covering said core with a component that has a pharmaceutically acceptable additive incorporated in at least one base selected from among fumaric acid and DL-tryptophan and which is substantially free from the drugs the release of which is to be controlled and thereby forming a shape of a dual structure;

said step A being optionally followed by the following step B, or the following steps B and C, or the following steps B–D, or the following steps B–E:

B. covering or overlaying the shape of a dual structure with a component containing at least one drug the release of which is to be controlled and thereby forming a drug release layer;

C. covering the shape obtained in said step B with a component that has a pharmaceutically acceptable additive incorporated in at least one base selected from among fumaric acid and Dl-tryptophan and which is substantially free from the drugs the release of which is to be controlled and thereby forming a release control layer;

D. covering or overlaying the shape obtained in said step C with a component containing at least one drug the release of which is to be controlled and thereby forming a drug release layer; and E. repeating said step C of forming a release control layer and said step D of forming a drug release layer at least once to produce the desired controlled-release formulation which satisfies the following conditions:

(1) the core be located in the innermost portion of the controlled-release formulation;

(2) said formulation have at least one release control layer covering the core, with at least one additional release control layer and/or drug release layer being optionally present;

(3) the release control layer(s) alternate with the drug release layer(s);

(4) the outermost layer may be either the release control layer or the drug release layer;

(5) if the outermost layer is the drug release layer, it may cover all or part of the surface of the underlying release control layer;

(6) the drugs to be contained in the core and the drug release layer of said formulation should be selected independently of each other;

(7) the core and the drug release layers may be formulated to permit immediate release or slow release of the drugs contained; and (8) if two or more drugs are to be contained in the core and the drug release layer(s) of said formulation, said core and a single drug release layer may each be composed of more than one layer containing only one drug.

10. The process according to claim 9, wherein the release control layer(s) and the drug release layer(s) are formed by means of a tablet machine or a coating machine.

11. The process according to claim 9, which is used to produce a solid preparation.

12. The process according to claim 10, which is used to produce a tablet.

13. The process according to claim 9, which is used to produce a formulation containing an immediate-release portion.

14. The process according to claim 13, which is used to produce a formulation whose core comprises the immediate-release portion.

15. The process according to claim 13, which is used to produce a formulation wherein the immediate-release portion contains a different drug from the drug the release of which is to be controlled.

16. The process according to claim 9, which is used to produce a formulation wherein the drug the release of which is to be controlled is nicorandil.

17. The process according to claim 9, which is used to produce a formulation wherein the base is fumaric acid.

18. The process according to claim 9, which is used to produce a formulation wherein the base is Dl-tryptophan.

19. The controlled-release formulation according to claim 1 wherein the drug the release of which is to be controlled is nicorandil.

* * * * *